US005607412A

United States Patent [19]
Brown

[11] Patent Number: 5,607,412
[45] Date of Patent: Mar. 4, 1997

[54] OSTOMY BAG COVER

[76] Inventor: E. Belle Brown, 21 S. St., Camillus, N.Y. 13031

[21] Appl. No.: 471,011

[22] Filed: Jun. 6, 1995

[51] Int. Cl.$^6$ ..................................................... A61F 5/44
[52] U.S. Cl. .................... 604/332; 604/345; 2/46
[58] Field of Search .................... 604/332, 345, 604/350–353; 2/46

[56] References Cited

U.S. PATENT DOCUMENTS

| | | | |
|---|---|---|---|
| D. 270,091 | 8/1983 | Setzer | D24/58 |
| D. 328,953 | 8/1992 | Garcia | D24/127 |
| D. 331,460 | 12/1992 | Mulder | D24/127 |
| 4,122,851 | 10/1978 | Grossner | 604/353 |
| 4,331,148 | 5/1982 | Steer et al. | 128/283 |
| 4,439,191 | 3/1984 | Hogan | 604/332 |
| 4,519,797 | 5/1985 | Hall | 604/332 |
| 4,705,512 | 11/1987 | Faucher | 604/332 |
| 4,738,661 | 4/1988 | Marut | 604/179 |
| 5,026,362 | 6/1991 | Willett | 604/345 |
| 5,135,520 | 8/1992 | Beaupied | 604/345 |
| 5,248,308 | 9/1993 | von Emster | 604/337 |

OTHER PUBLICATIONS

Hollister Product Data Sheet, Ostomy Drainable Pouches, 1982.

Primary Examiner—John G. Weiss
Assistant Examiner—Rob Clarke
Attorney, Agent, or Firm—Trapani & Molldrem

[57] ABSTRACT

An ostomy bag cover is formed of a single piece of a soft knit fabric, folded and sewn so that there are no rough edges in contact with the patient. The cover contains the ostomy bag and isolates the patient from direct contact of the plastic bag with the skin. The cover has a distal side panel and left and right proximal side panels that meet at a vertical midline on the patient side of the cover. The panels are left detached from one another from the top seam partway down the midline to define a vertical slot through which the fitting or flange of the ostomy bag protrudes. Another slot is provided along the bottom seam to accommodate a drain tube.

8 Claims, 2 Drawing Sheets

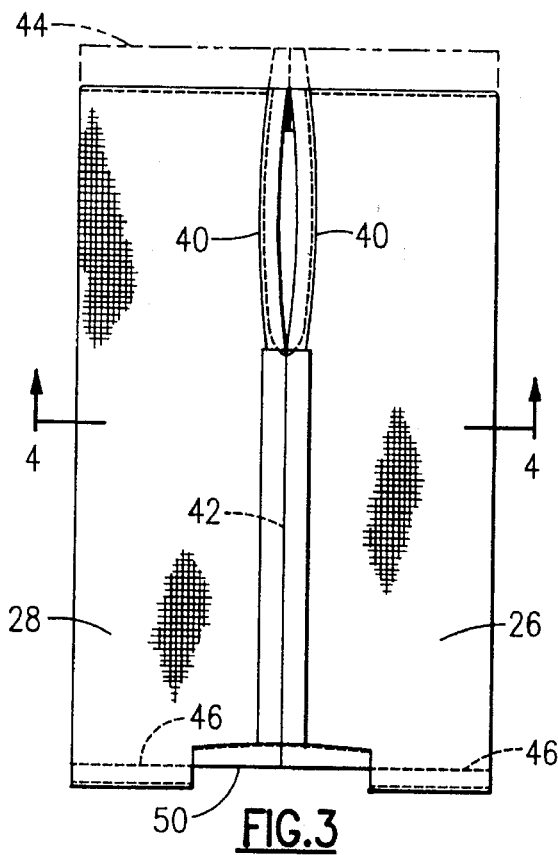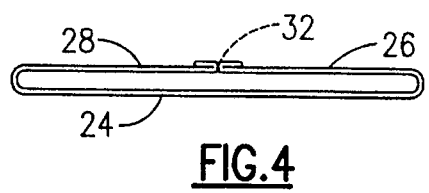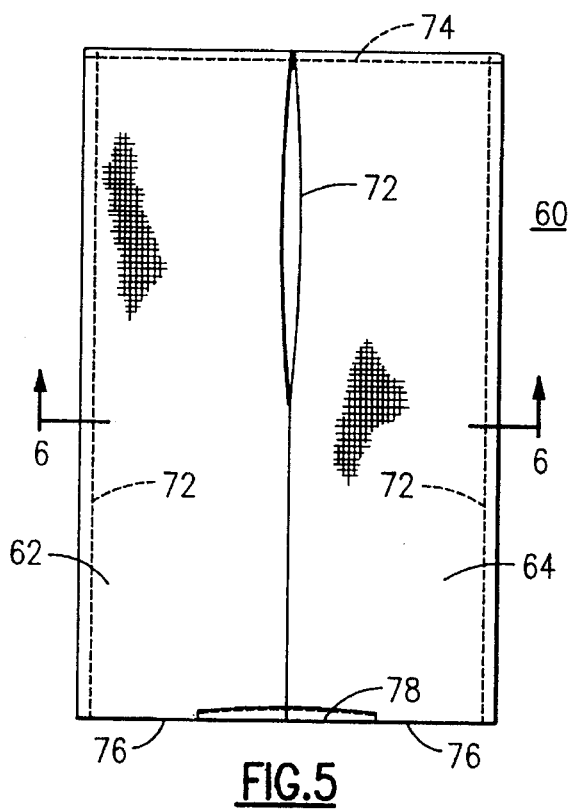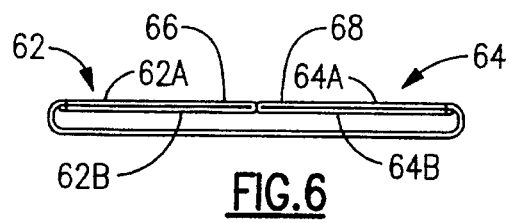

OSTOMY BAG COVER

BACKGROUND OF THE INVENTION

This invention relates to ostomy appliances, that is to collection pouches and like devices that are required to be worn by ostomy patients, and is more particularly directed to garments and covers for supporting and holding ostomy appliances. The invention is specifically directed to a case or cover to prevent discomfort from direct contact of a colostomy bag or pouch with the skin of the patient.

A surgical procedure known as colostomy is performed on persons in whom some portion of their large intestine has become inoperative due to disease or injury. A passageway, or stoma, is surgically formed on the patient through the abdominal wall, and the intestine is re-routed to the stoma. Waste material exits the body through this stoma, and a collection bag or appliance is attached to receive the waste material. There are a variety of collection bags in common use, but these all typically are made of a transparent or semitransparent plastic material, and have a flange or fitting at the upper part of the bag to fasten removably to the stoma. In most cases, at the bottom of the collection bag there is a drain tube that can be opened to release fluid wastes.

There is some discomfort involved in the wearing of a colostomy bag. The bag itself is made of a plastic material, and this can irritate the patient's skin if in direct contact. Also, the bag can be somewhat cold to the touch when attached and warm to hot as it fills, and thus can be rather uncomfortable. The plastic material can also stick to the skin.

Because small leaks can develop in ostomy bags, it is often useful to provide a cover which can absorb some liquid, so that in case of a leak the risk of embarrassment and damage to the patient's clothing can be minimized.

A number of covers for collection bags of this type have been previously proposed. However, these have often been complex or difficult to install, or have required additional apparatus. In many cases, the covers have left significant portions of the colostomy bag uncovered, and in physical contact with the patient.

The term "ostomy" comprehends both colostomy and ileostomy (which involves the small intestine). In both conditions, collection pouches are used, and in both conditions there are similar problems of discomfort. Similar bags are also used for urine collection.

Examples of prior ostomy bag covers are described in U.S. Pat. No. 4,705,512, to Faucher; U.S. Pat. No. 4,439,191 to Hogan; U.S. Pat. No. 4,331,148 to Steer et al.; U.S. Pat. No. 4,519,797 to Hall; U.S. Pat. No. 5,248,308 to von Emster; U.S. Pat. No. 5,026,352 to Willett; and U.S. Pat. No. 5,135,520 to Beaupied. Additional examples are shown in U.S. Design patents Nos. Des. 331,460; Des. 328,953; and Des. 270,091. Despite these prior covers, there has been a lingering need for a cover of simple design that would be economical to make and easy to employ, and which would eliminate as much of the discomfort as possible associated with the wearing of an ostomy appliance of this type.

OBJECTS AND SUMMARY OF THE INVENTION

Accordingly, it is an object of the present invention to provide a cover for an ostomy collection bag which increases wearer comfort and avoids the drawbacks of the prior art.

It is another object to provide an ostomy bag cover that is of a straightforward, one-piece design, and which is simple to install and replace, and yet covers the bag completely.

It is a more specific object to provide an ostomy bag cover that is made entirely of a soft, knit material and has only soft edges in contact with the patient.

In accordance with one aspect of the present invention, an ostomy bag cover is formed of a single piece of a flexible, knit material, preferably combed cotton or cotton blend of the type that is frequently used in men's and women's undergarments. The material is folded and sewn so that there is a distal panel that covers the side of the bag away from the patient and a pair of proximal panels that together cover the proximal or patient side of the ostomy bag. The two proximal panels meet at a vertical midline. The cover is sewn at the top and bottom, and the two proximal panels are sewn together along a lower part of the vertical midline. The proximal panels are leer detached from one another from the top seam to a point partway down the midline so as to form a vertical slit. The flange or fitting of the ostomy bag protrudes through this slit. The left and right proximal panels are joined to one another below this point. In order to accommodate the drain tube that is usually provided on the ostomy bag, a lower slit, typically about four cm in length, is left in the central part of the bottom seam. Preferably, the seams are blind-sewn, that is sewn through with the cover inside out, so that in the finished cover there are no unfinished edges on the outside of the cover in contact with the patient. In one embodiment, the panels are single thickness, and rolled seams are formed along the slits. In another embodiment, the left and right proximal panels are folded over so as to be double thickness panels. This creates additional cushioning and thermal insulation for increasing comfort, and also increases the absorbent capacity in the event of minor leakage.

The ostomy bag covers of this invention are laundrable, and can be kept clean and sanitary. Suitable fasteners, such as snaps or Velcro, can be added to attach the ostomy bag covers to the patient's undergarments or to another support device. In addition, these covers can be sewn in place into the patient's undergarments, if desired, providing maximum support and comfort.

The above and many other objects, features, and advantages of this invention will be more fully appreciated from the ensuing description of a preferred embodiment, which is to be read in conjunction with the accompanying Drawing.

BRIEF DESCRIPTION OF THE DRAWING

FIG. 3 is an elevational view of the cover of this embodiment here turned inside out to show the seams on the patient- or proximal side.

FIG. 4 is a cross sectional view of this embodiment taken at 4—4 of FIG. 3.

FIG. 5 is an elevational view of a cover according to an alternative embodiment, showing the proximal or patient side thereof.

FIG. 6 is a cross sectional view of this embodiment taken at 6—6 of FIG. 5.

DETAILED DESCRIPTION OF THE PREFERRED EMBODIMENT

Figure 1:
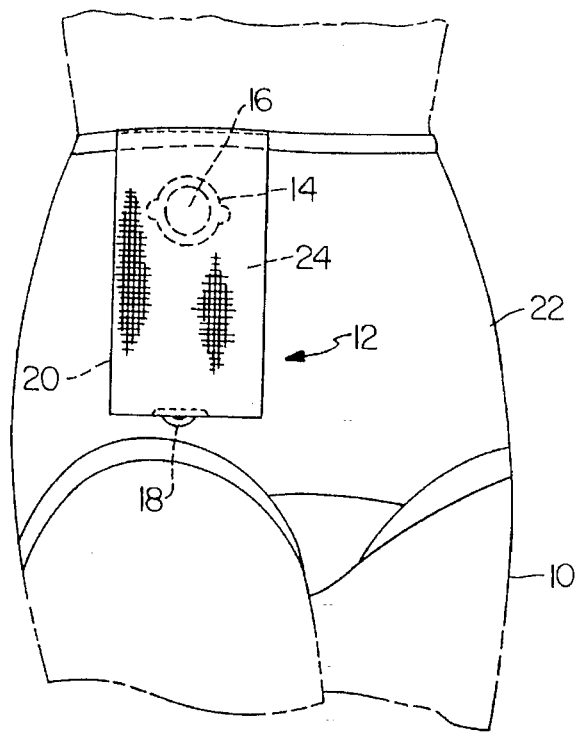
FIG. 1 is a perspective view of an ostomy bag being worn by an ostomy patient, here shown together with a cloth cover according to an embodiment of the present invention.
Figure 2:
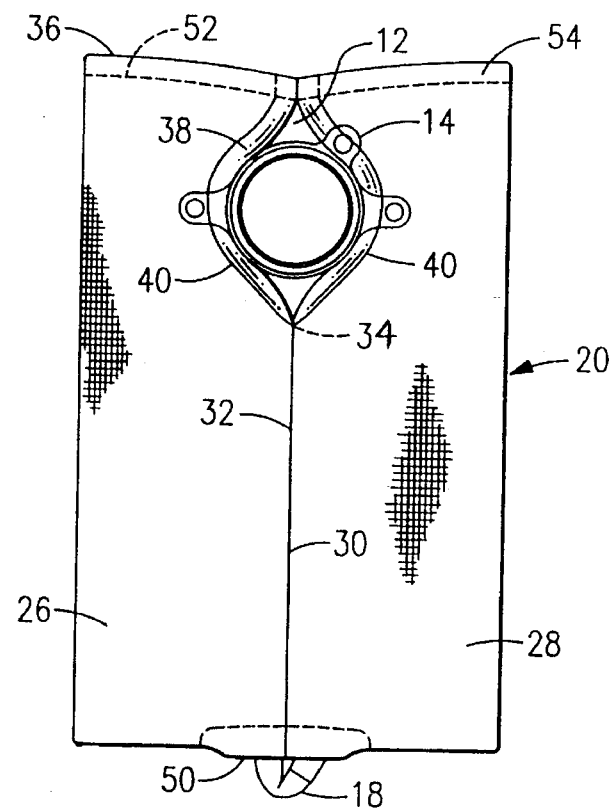
FIG. 2 is an elevational view of the ostomy bag cover of this embodiment showing the patient- or proximal side thereof, and containing an ostomy bag therein.

With reference now to the Drawing, FIG. 1 shows an ostomy patient 10 wearing an ostomy bag or pouch 12. The bag 12, shown in more detail in FIG. 2, is made of a clear or transparent plastic film and has a fitting or flange 14 on its upper portion which is secured to a stoma 16 on the patient's abdomen. A drain tube 18 is provided at the bottom of the bag 12 for withdrawing liquid or fluid wastes from the bag 12. The drain tube has a closure or stopper that can be removed to permit drainage of the bag 12. As shown, the bag is contained and concealed inside a fabric cover 20. The cover 20 is made entirely of a soft, absorbent cloth, and in this embodiment a combed cotton knit fabric is used. This is the same material that is often used in undergarments, e.g. tee shirts, and has a high degree of wearer comfort. The material can also be easily laundered and kept clean and sanitary. In this case, the ostomy bag 12 and cover 20 are worn inside an undergarment 22, but optionally the cover 20 could be incorporated into the patient's undergarment.

As shown in FIG. 2, with further reference to FIGS. 3 and 4, the ostomy bag cover 20 is made from a single rectangle of material cut about eleven inches by about thirteen inches. The cover is formed of an outer or distal panel 24 (FIG. 1) that covers the side of the bag 12 away from the patient, and left and right proximal panels 26 and 28, that meet at a vertical midline 30 to cover the proximal or patient side of the ostomy bag 12. The two proximal panels 26, 28 are joined by a stitched seam 32 below a point 34 partway down from a top seam 36 of the cover. A vertical slot 38 or opening about eight cm in length remains between the top seam 36 and the point 34. This slot provides access for installing the ostomy bag 12 inside the cover 20, and also permits the fitting or flange 14 to protrude. As shown in FIGS. 3 and 4, a rolled seam 40 is formed on each side of the slot 38. A blind seam 42 is stitched (by sewing on the reverse side) to form the seam 32 below the slot 38. A blind stitched seam 44 is stitched at the top of the cover, and another blind stitched seam 46 is made at the bottom. This seam 46 is stitched in two parts, separated from one another leaving a central portion, i.e. the parts of the right and left proximal panels 26 and 28 near the midline 30, detached from the distal panel 22 to define a central slot 50. This slot 50 is about four centimeters in length, and provides access to the drain tube 16, so that accumulated waste can be withdrawn from the bag 12 without removing the cover 20. Rolled edges are also formed at the central slot.

After the cover is turned right side out, an additional stitched line 52 is sewn through parallel to the top seam 44. This defines a top flap 54, which can be used for attachment to a support belt or undergarment, if desired.

A cover 60 according of an alternative embodiment of the present invention is illustrated in FIGS. 5 and 6. This embodiment is similar to that of the first embodiment, and only the differences will be discussed in detail. Here, the proximal or patient side of the cover 60 is double thickness, formed of two layers of the combed cotton knit material. In this cover 60, left and right proximal panels 62 and 64 are each formed by folding the material so that there are an outer layer 62A, 64A and an inner layer 62B, 64B. The proximal panels 62, 64 have respective bends 66, 68 that meet at a vertical midline 70. Stitching 72 near the left and right edges joins the outer layers 62A and 64A to the respective inner layers 62B and 64B. A vertical slot 74 is formed at the vertical midline, as in the previous embodiment, extending partway down from a top seam 74. Also, at a bottom seam 76, a slot 78 is provided for access to the drain tube.

In both embodiments, the cover is positioned between the patient and the bag to prevent contact and help avoid skin irritation from contact with the plastic film, and discomfort due to heat or cold. The knit cloth material is soft, flexible, breathable, and absorbent, has an expansion capacity, and a natural feel to the patient. Because of the oblong shape and the simplicity of design, the ostomy bag covers can be made in quantity with minimal or zero waste of material. Computerized sewing equipment can be easily adapted and programmed for automatic production of these covers.

While the invention has been described with reference to specific preferred embodiments, the invention is certainly not limited to those precise embodiments. Rather, many modifications and variations will become apparent to persons of skill in the art without departure from the scope and spirit of this invention, as defined in the appended claims.

I claim:

1. A cover for an ostomy bag of the type which has a proximal side facing an ostomy patient and a distal side facing away from the patient, with a fitting on an upper portion of the proximal side that engages a stoma that has been surgically attached to the patent's abdomen and with a releasably closed drain tube at a lower end of the ostomy bag; the cover being formed of a single piece of a flexible, knit material and comprising a distal panel and left and right proximal panels unitary with said distal panel forming seamless left and right edges, and with said proximal panels meeting at a vertical midline; said distal panel and proximal panels being sewn together at the top and bottom edges thereof to form a top seam and a bottom seam, respectively, of said cover; said proximal panels forming a vertical slit along said midline from said top to a predetermined point on said proximal midline, said vertical slit being openable to permit insertion and removal of the ostomy bag through the slit, and conforming around the fitting of the ostomy bag such that said fitting projects proximally through said slit; said left and right proximal panels being joined below said predetermined point to form a vertical seam; and a slit below said predetermined point for access to said drain tube.

2. The ostomy bag cover of claim 1 wherein said top seam, said bottom seam, and said vertical seam are blind-sewn such that there are no unfinished edges on the outside of said cover in contact with said patient.

3. The ostomy bag cover of claim 1 wherein said bottom seam includes a central slit for access to said drain tube.

4. The ostomy bag cover of claim 3 wherein said central slit is about four centimeters in length.

5. The ostomy bag cover of claim 3 wherein said bottom seam is straight and horizontal, and said central slit occupies a central portion thereof straddling said central midline.

6. The ostomy bag cover of claim 1 wherein said left and right proximal panels are folded over so as to be double thickness panels.

7. The ostomy bag cover of claim 1 wherein said cover is formed of a single rectangle of said flexible, knit material.

8. The ostomy bag cover of claim 7 wherein said rectangle is dimensioned approximately eleven by thirteen inches.

* * * * *